(12) United States Patent
Tedesco et al.

(10) Patent No.: US 8,824,042 B2
(45) Date of Patent: Sep. 2, 2014

(54) ELLIPSOIDAL RAMAN SIGNAL AMPLIFIER

(75) Inventors: James M. Tedesco, Livonia, MI (US); Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 183 days.

(21) Appl. No.: 13/564,461

(22) Filed: Aug. 1, 2012

(65) Prior Publication Data
US 2014/0036347 A1 Feb. 6, 2014

(51) Int. Cl.
*H01S 3/30* (2006.01)
*G02B 5/10* (2006.01)

(52) U.S. Cl.
USPC ............................. 359/334; 359/346; 359/858

(58) Field of Classification Search
USPC ................................ 359/334, 346, 3, 858, 868
See application file for complete search history.

(56) References Cited

U.S. PATENT DOCUMENTS

| | | | |
|---|---|---|---|
| 3,704,951 A | 12/1972 | Chupp | |
| 3,825,325 A | 7/1974 | Hartley et al. | |
| 4,161,351 A * | 7/1979 | Thomas et al. | 359/853 |
| 4,179,192 A * | 12/1979 | Shafer | 359/858 |
| 4,281,924 A | 8/1981 | Auer et al. | |
| 6,123,436 A * | 9/2000 | Hough et al. | 362/296.06 |
| 6,721,049 B1 | 4/2004 | Gupta et al. | |
| 7,671,985 B1 | 3/2010 | Milosevic et al. | |
| 2003/0223063 A1 | 12/2003 | Hill et al. | |
| 2007/0010727 A1 | 1/2007 | Van Beek et al. | |

* cited by examiner

*Primary Examiner* — Eric Bolda
(74) *Attorney, Agent, or Firm* — Gifford, Krass, Sprinkle, Anderson & Citkowski, P.C.

(57) ABSTRACT

Raman signal amplification apparatus comprises an ellipsoidal reflector providing a first real focus f1, and second real or virtual focus f2, both foci being situated within a sample volume. When an input laser excitation beam having an initial numerical aperture (NA) is focused onto one of the foci, the beam is reflected by the reflector and refocused onto alternating foci, such that the NA of the reflected optical path progressively increases for higher efficiency collection of Raman emissions from the multiple foci. The ellipsoidal reflector may be a half section providing a single real focus f1, with a flat reflector producing a mirror image of the ellipsoidal reflector, such that f2 is a virtual focus occupying the same point as f1. Alternatively, the ellipsoidal reflector may have a first half section with a first real focus f1 and a second half section with a second real focus f2.

6 Claims, 4 Drawing Sheets

ELLIPSOIDAL RAMAN SIGNAL AMPLIFIER

FIELD OF THE INVENTION

This invention relates generally to Raman spectroscopy and, in particular, to a Raman signal amplifier based upon ellipsoidal reflection to enhance collection efficiency.

BACKGROUND OF THE INVENTION

When taking Raman spectra of gases or other nominally transparent fluids it is desirable to generate as much signal as possible. Several techniques have been developed to increase these signal levels. One approach, described in U.S. Pat. No. 5,956,138, relies on multipass techniques that produce a multiplicity of focal images. Another approach, disclosed in U.S. Pat. No. 7,692,786 uses retro reflections. Each copy of the focal image adds to the overall signal level and controls signal level.

Certain proposed Raman systems use ellipsoidal reflectors, since rays passing through one point are directed to the other. However, the ellipsoidal reflectors in existing systems are typically used for beam redirection as opposed to signal amplification. For example, U.S. Pat. No. 3,704,951 uses mirrors, which may be ellipsoidal, in such relation to a sample zone that source light is caused to pass many times through a sample in that zone for increasing substantially the intensity level of Raman light emission from the sample. However, the multiple "bounces" of the light are limited to illumination and not collection, which is derived form a separate lateral path. The emphasis is on providing a multi-pass "pencil beam" from a laser, and not magnification of numerical aperture.

Similarly, U.S. Pat. No. 3,825,325 uses a collimated pencil beam or ray of light to multi-pass at one focus of an ellipsoid for lateral collection. Numerical aperture is actually diminished. In U.S. Pat. No. 6,721,049, an ellipsoid is used as a single-reflection imager, not a multi-bounce re-image amplifier. Published U.S. Application Serial No. 2007/0010727 is directed to a catheter head having means for directing of radiation to a blood detection volume, means for receiving of return radiation from the blood detection volume, and means for transmitting of the return radiation to means for analysis of the return radiation for determination of at least one property of the blood. One embodiment comprises a spherical mirror for reflection of the laser radiation back into the blood detection volume, and an ellipsoidal mirror, wherein the blood detection volume includes one of the focal points of the ellipsoidal mirror. However, the ellipsoid is used to image a fiber, and not to trap/form re-imaging for amplification and/or low noise.

SUMMARY OF THE INVENTION

This invention resides in a Raman signal amplifier based upon ellipsoidal reflection to enhance both laser excitation and signal collection efficiency. Raman signal amplification apparatus according to the invention comprises an ellipsoidal reflector providing a first real focus f1, and second real or virtual focus f2, both foci being situated within a sample volume. The optical arrangement is such that when an input laser excitation beam having an initial numerical aperture (NA) is focused onto one of the foci, the beam is reflected by the reflector and refocused onto alternating foci, such that the NA of the reflected optical path progressively increases for higher efficiency collection of Raman emissions from the multiple foci.

In accordance with one preferred embodiment, the ellipsoidal reflector is a half section providing a single real focus f1, with a flat reflector producing a mirror image of the ellipsoidal reflector, such that f2 is a virtual focus occupying the same point as f1. According to an alternative preferred embodiment, the ellipsoidal reflector has a first half section with a first real focus f1 and a second half section with a second real focus f2. In in case, the laser excitation beam is focused directly onto one of the foci without undergoing any reflections, with the first reflection of the beam occurring off of the section of the ellipsoidal reflector associated with the other focus.

The input beam may be focused onto one of the foci with a lens or parabolic or other conic section reflector. The apparatus may include a spherical mirror having a radius of curvature corresponding to f2, thereby achieving a counter-propagating beam that undergoes a fixed number of alternating focuses within the sample volume.

DETAILED DESCRIPTION OF THE INVENTION

Figure 1:
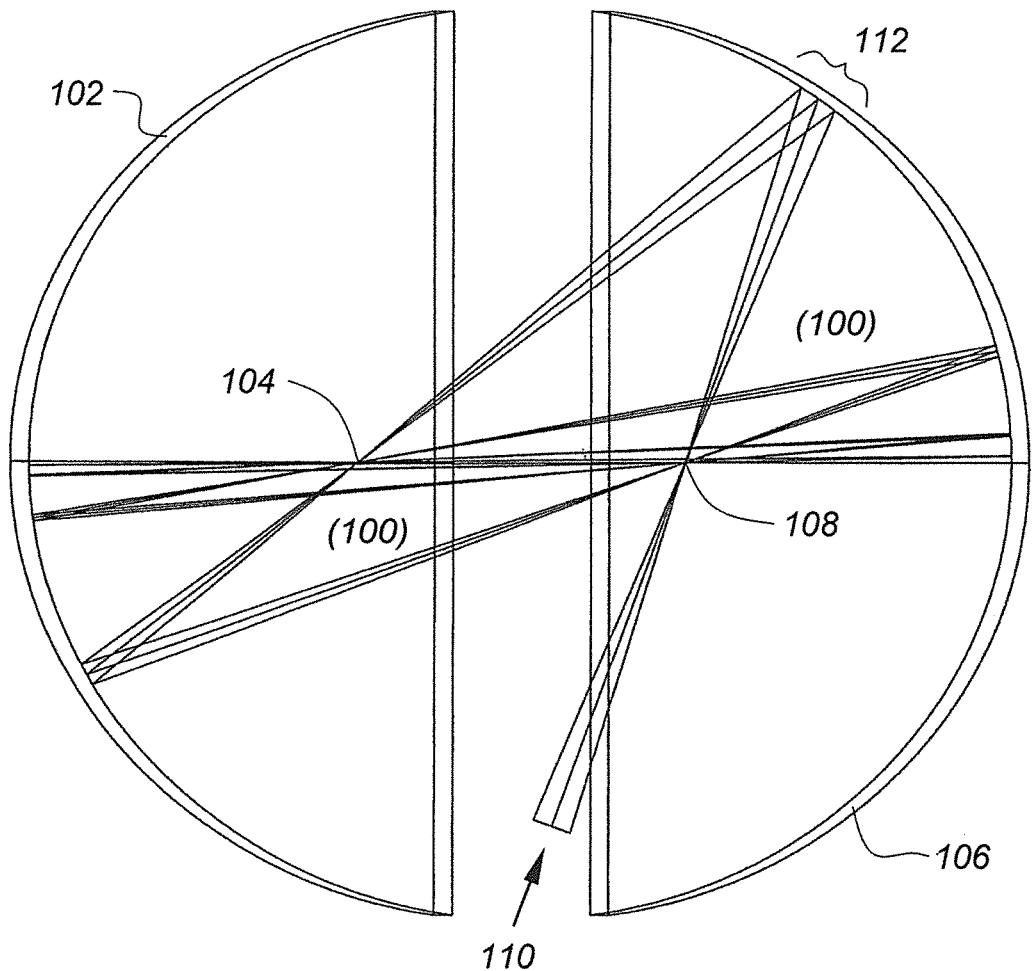
FIG. 1 is a cross-sectional diagram that illustrates a non-preferred configuration using an ellipsoidal reflector.

FIG. 1 is a cross-sectional diagram that illustrates the use of an ellipsoidal reflector as a Raman signal acquisition system. The focused input represents a common excitation/collection path from a generic Raman probe "head" and focusing element. This configuration is not preferred for reasons that will soon be apparent. The ellipsoidal reflector includes a first half section 102 with a first focus 104 and a second half section 106 having a second focus 108. The major optical axis is the line intersecting both foci. Although the drawing is shown in two dimensions, it should be kept in mind that the reflectors 102, 106 include three-dimensional ellipsoidal surfaces, either in the form of full ellipsoid sections or ellipsoidal "strips" if precise ray tracings are known in advance. A stock NT90-973 ellipsoidal reflector applicable to the invention may be obtained from Edmund Scientific Corp. All reflectors associated with the various embodiments comprise first-surface mirrors.

The invention is applicable to any gaseous or liquid sample of sufficient transparency to accommodate the transmission described herein. In FIG. 1, the volume 100 containing a sample under investigation is assumed to be between the reflectors 102, 106, such that both foci are within the sample. The input laser excitation beam 110 is focused onto focus 108 associated with reflector 106. Note that by illuminating the focus closest to the "first bounce" half (at 112), the numerical aperture of the path diminishes as the light focuses to a progressively larger conjugate as the reflected beam approaches the major axis. Such a configuration is probably not any better than the use of an unfocused beam in the sample volume as each bounce produces diminishing collected signal returns due to the diminishing collection numerical aperture of the common excitation/collection path.

Figure 2:
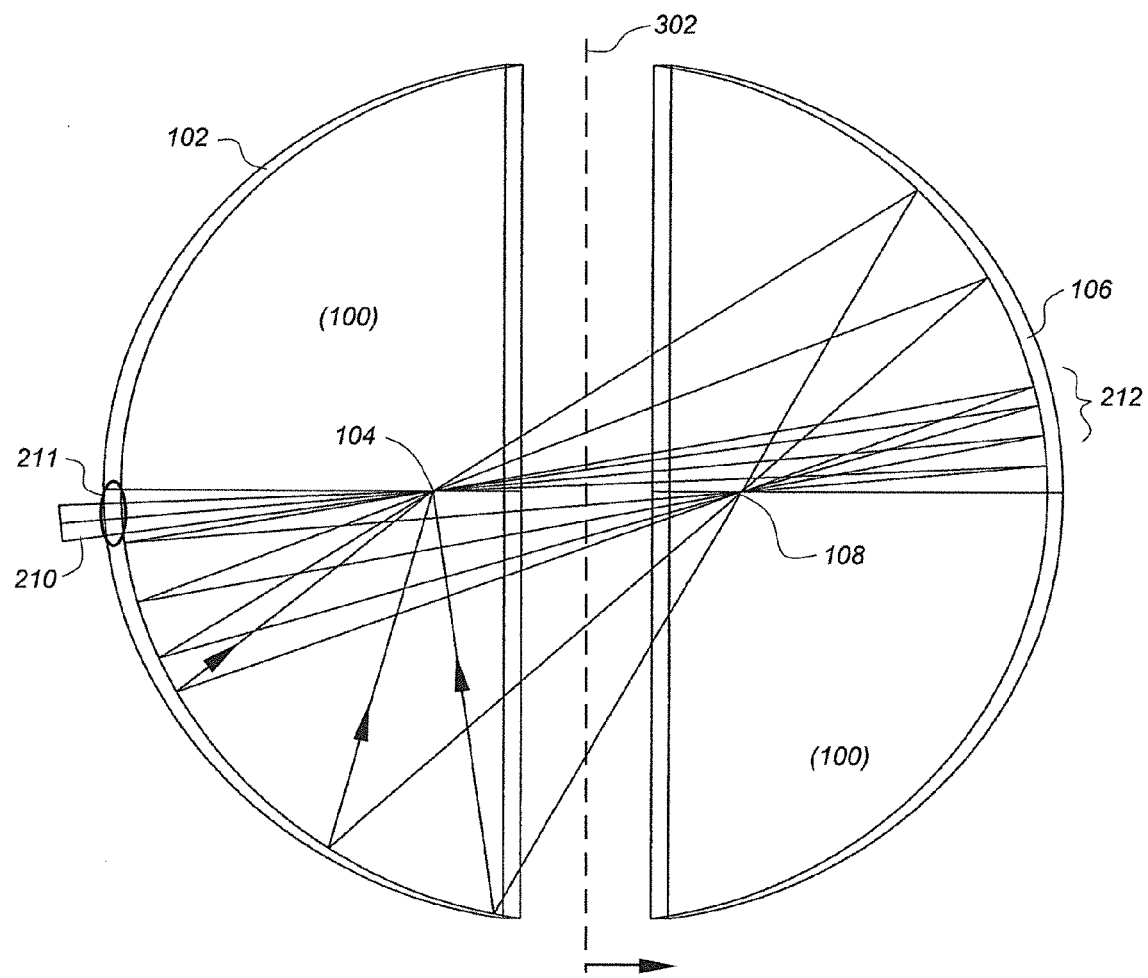
FIG. 2 is a cross-sectional diagram that illustrates a first preferred configuration according to the invention.

FIG. 2 is a cross-sectional diagram that illustrates a first preferred configuration according to the invention. The physical setup is identical to that shown in FIG. 1 with the exception that the input excitation beam 210 is now focused onto a focus farthest from the first bounce 212. In other words, reflector 106 is behind focus 104. The common excitation/collection path 210 is shown entering the volume near the major axis, perhaps through a small port 211, through this is not necessary so long as the first bounce is associated with the opposite half ellipsoidal section. Note that with this change, the numerical aperture of the beam grows very rapidly with each reflection and refocusing, such that significant amplification is achieved after only a few bounces.

Figure 3:
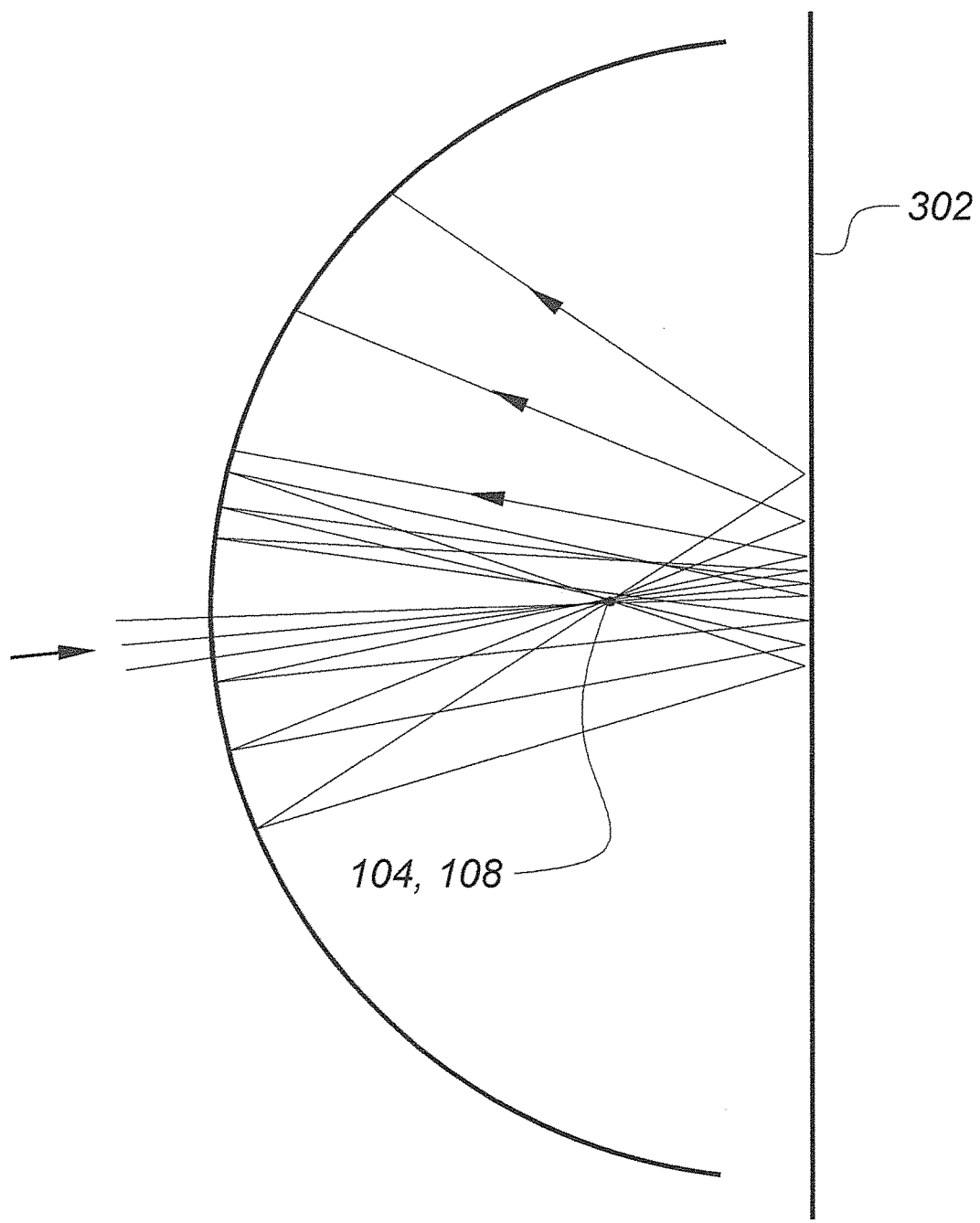
FIG. 3 is a cross-sectional diagram that illustrates a second preferred configuration.

As shown in FIG. 3, a flat mirror may be placed along plane 302, thereby producing the same optical configuration as that of FIG. 2 but without the need for a full ellipsoid with two real foci which may be more expensive. One of skill in the art will appreciate that placement of reflector 302 precisely between the foci of FIG. 2 and perpendicular to the major axis produces a mirror image of reflector 102 and a virtual second focus 106 that occupies the same point as real focus 104; otherwise, operation is essentially identical.

Figure 4:
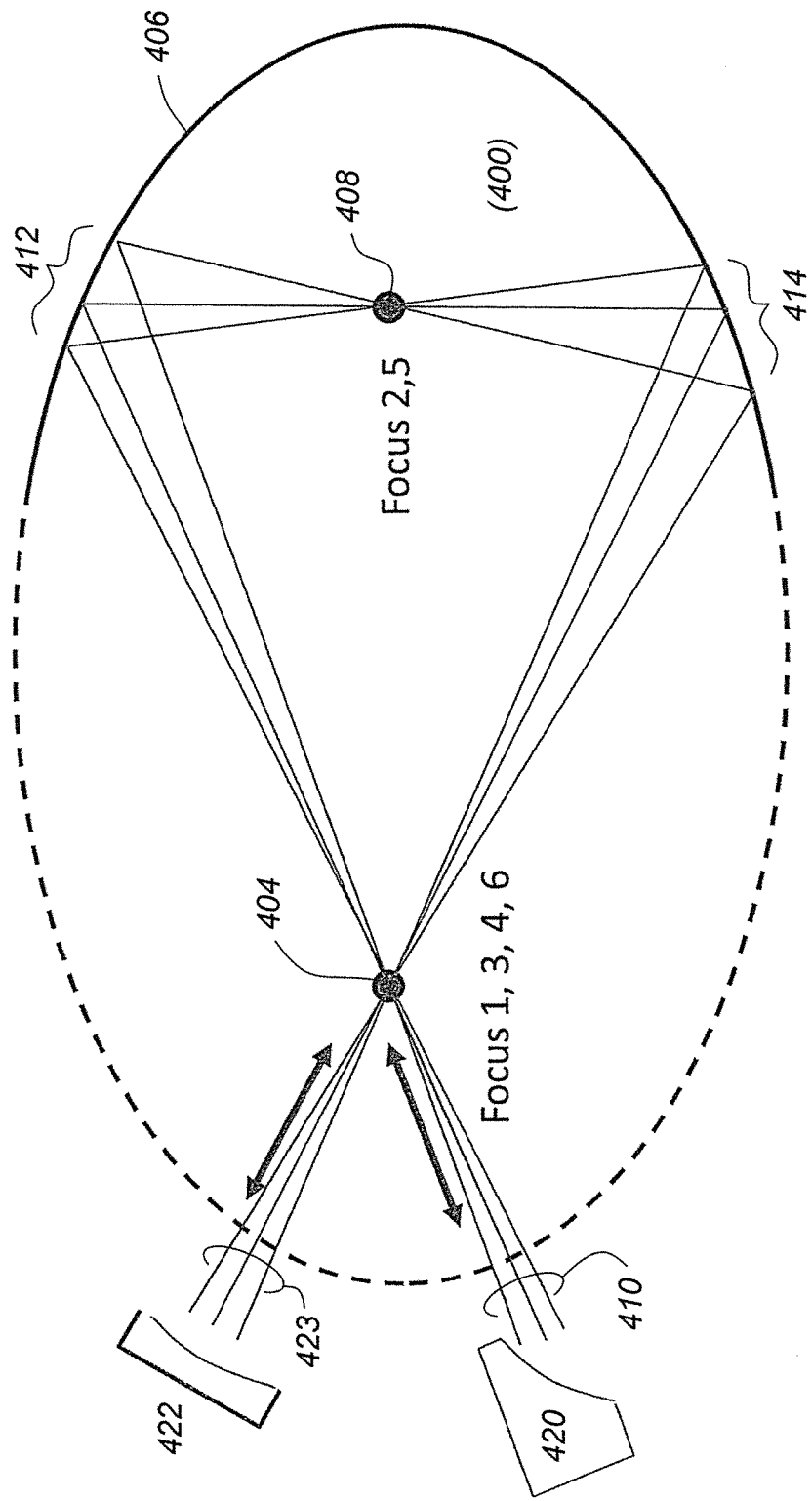
FIG. 4 is a cross-sectional diagram that illustrates the use of a retro reflector to set the number of passes through an ellipsoidal reflector.

Optics may be provided to produce a counter-propagating path with a predetermined number of focuses as shown in FIG. 4. Here the input beam 410 is delivered via an off-axis parabola 420 similar to the arrangement shown in U.S. Pat. No. 7,692,786, the entire content of which is incorporated herein by reference. The beam is focused onto point 404, reflected off ellipsoidal reflector 406 at 412, and focused onto focal point 408. The beam is then reflected again at region 414, focused at 404 and retro-reflected with spherical mirror 422, also discussed in the '786 patent, which has a radius of curvature that coincides with point 404. Thus, in the arrangement of FIG. 4, the focusing of the input beam 410 and placement of mirror 422 creates a virtual second ellipsoid focus and a six-focus amplification scheme. Such an arrangement may be advantageous insofar as a single ellipsoidal reflector is required and ports for the beams 410, 423 may be more conveniently provided relative to sample volume 400. The use of focusing mirror 420 (along with the upstream optical components of the gas probe in the patent '786 is also the preferred way of forming the focused input paths shown in FIGS. 2 and 3, though such components are not shown in those figures.

The invention claimed is:

1. Raman signal amplification apparatus, comprising:
    an ellipsoidal reflector providing a first real focus f1, and second real or virtual focus f2, both foci being situated within a sample volume;
    whereby, when an input laser excitation beam having an initial numerical aperture (NA) is focused onto one of the foci, the beam is reflected by the reflector and refocused onto alternating foci, such that the NA of the reflected optical path progressively increases for higher efficiency collection of Raman emissions from the multiple foci.

2. The Raman signal amplification apparatus of claim 1, wherein:
    the ellipsoidal reflector is a half section providing a single real focus f1; and
    a flat reflector that produces a mirror image of the ellipsoidal reflector, such that f2 is a virtual focus occupying the same point as f1.

3. The Raman signal amplification apparatus of claim 1, wherein the ellipsoidal reflector has a first half section with a first real focus f1 and a second half section with a second real focus f2.

4. The Raman signal amplification apparatus of claim 1, wherein:
    the ellipsoidal reflector defines a first half section with a first real focus f1, and a second half section with a second real or virtual focus f2;
    the laser excitation beam is focused directly onto one of the foci without undergoing any reflections; and
    the first reflection of the beam occurs off of the section of the ellipsoidal reflector associated with the other focus.

5. The Raman signal amplification apparatus of claim 1, wherein the input beam is focused onto one of the foci with a lens or parabolic or other conic section reflector.

6. The Raman signal amplification apparatus of claim 1, including a spherical mirror having a radius of curvature corresponding to f2, thereby achieving a counter-propagating beam that undergoes a fixed number of alternating focuses within the sample volume.

* * * * *